US011307202B1

United States Patent
Abdelhadi et al.

(10) Patent No.: US 11,307,202 B1
(45) Date of Patent: *Apr. 19, 2022

(54) ANTIBODY BINDING DETECTION METHOD FOR DETECTING MERS-COV

(71) Applicant: King Abdulaziz University, Jeddah (SA)

(72) Inventors: Ayman Talaat Abbas Abdelhadi, Jeddah (SA); Esam Ibraheem Ahmed Azhar, Jeddah (SA); Sherif Aly Abdelkhalek Elkafrawy, Jeddah (SA); Sayed Sartaj Sohrab, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/406,182

(22) Filed: Aug. 19, 2021

Related U.S. Application Data

(63) Continuation of application No. 17/207,063, filed on Mar. 19, 2021, now Pat. No. 11,131,672, which is a continuation of application No. 17/161,820, filed on Jan. 29, 2021.

(51) Int. Cl.
  *G01N 33/569* (2006.01)
  *G01N 33/543* (2006.01)
  *C07K 16/10* (2006.01)
  *A61K 39/215* (2006.01)

(52) U.S. Cl.
  CPC ..... *G01N 33/56983* (2013.01); *A61K 39/215* (2013.01); *C07K 16/10* (2013.01); *G01N 33/54386* (2013.01); *C07K 2317/30* (2013.01); *C07K 2317/34* (2013.01); *C12N 2770/20011* (2013.01); *G01N 2333/165* (2013.01)

(58) Field of Classification Search
  CPC .......... A61K 2039/505; A61K 47/6849; A61K 38/1774; A61K 39/12; C07K 2317/622; C07K 2317/55
  See application file for complete search history.

(56) References Cited

FOREIGN PATENT DOCUMENTS

| | | |
|---|---|---|
| JP | 2017-6008 A | 1/2017 |
| JP | 2017-145246 A | 8/2017 |
| KR | 10-1782862 B1 | 9/2017 |
| WO | WO 2016/080701 A1 | 5/2016 |

OTHER PUBLICATIONS

Alan, "Ostrich Antibodies to Fight Resistant Infections", https://sciencebusiness.technewslit.com/?p=30007#, Dec. 5, 2016, 2 pages.
Yasuhiro Tsukamoto, et al., "Protection against Infectious Bronchitis Virus, a Corona Virus Infection, Using Ostrich Antibodies", Health, Scientific Research Publishing, vol. 10, Oct. 12, 2018, pp. 1294-1308.
Aymn Talat Abbas, et al., "IgY antibodies for the immunoprophylaxis and therapy of respiratory infections", Human Vaccines & Immunotherapeutics, vol. 15, No. 1, 2019, pp. 264-275.
A. Palaniyappan, et al., "Diagnostics of severe acute respiratory syndrome-associated coronavirus (SARS-CoV) nucleocapsid antigen using chicken immunoglobulin Y", Poultry Science, vol. 91, 2012, pp. 636-642.
Zumla et al. Lancet, 2015, vol. 386 (9997), pp. 995-1007.

*Primary Examiner* — Bao Q Li
(74) *Attorney, Agent, or Firm* — Oblon, McClelland, Maier & Neustadt, L.L.P.

(57) ABSTRACT

A method for detecting MERS-CoV at high sensitivity and specificity using IgY antibodies that bind to MERS-CoV N protein, its fragments and domains. Isolated or purified IgY monospecific antibodies to MERS-CoV N protein.

14 Claims, 5 Drawing Sheets

Specification includes a Sequence Listing.

FIG. 3

ANTIBODY BINDING DETECTION METHOD FOR DETECTING MERS-COV

CROSS-REFERENCE TO RELATED APPLICATIONS

The present application is a Continuation of U.S. application Ser. No. 17/207,063, now allowed, having a filing date of Mar. 19, 2021 which is a Continuation of U.S. application Ser. No. 17/161,820, pending, having a filing date of Jan. 29, 2021.

REFERENCE TO A SEQUENCE LISTING

In accordance with 37 CFR § 1.52(e)(5), the present specification makes reference to a Sequence Listing (submitted electronically as a .txt file named "530967US_ST25.txt". The .txt file was generated on Jan. 25, 2021 and is 6.83 kb in size. The entire contents of the Sequence Listing are hereby incorporated by reference.

BACKGROUND OF THE INVENTION

Field of the Invention

The invention pertains to the fields of virology, and immunodiagnostic products and methods, more specifically, to the use of avian IgY antibodies to detect MERS-CoV nucleocapsid protein ("N protein") epitopes with high specificity and sensitivity.

Description of Related Art

Middle-East respiratory syndrome coronavirus (MERS-CoV) is an emerging zoonotic virus that causes severe respiratory illness in humans. MERS first emerged in Saudi Arabia in 2012 causing an epidemic in the Middle East. About 2,500 cases have been reported as of January 2020; worldwide web.emro.who.int/health-topics/mers-cov/mers-outbreaks.html. Retrieved Jan. 27, 2021. About 35% of those who are diagnosed with the disease die from it; worldwide web.who.int/news-room/fact-sheets/detail/middle-east-respiratory-syndrome-coronavirus-(mers-cov). Retrieved Jan. 27, 2021. Larger outbreaks have occurred in South Korea in 2015 and in Saudi Arabia in 2018. The World Health Organization (WHO) reports that there have been 2519 confirmed cases with a total of 866 deaths in 26 countries including the United States, and that the fatality rate is 34.3%; *MERS situation update*, January 2020. World Health Organization. January 2020. Respiratory infections by MERS-CoV represent a global threat that affects millions of people, especially the immunocompromised, children, and the elderly.

Dromedary camels represent an animal reservoir for MERS-CoV from which zoonosis can occur. The vast majority of dromedaries in the Arabian Peninsula are reported to be seropositive for MERS-CoV and MERS-CoV strains found in epidemiologically-linked humans and dromedary camels are almost identical; Azhar, E. I., et al., *Evidence for camel-to-human transmission of MERS coronavirus*. NEW ENGLAND JOURNAL OF MEDICINE, 2014, 370(26): 2499-2505. However, small outbreaks from countries outside Saudi Arabia such as the UK, Europe, USA, and China have provided evidence of human-to-human transmission.

Currently, there are no clinically approved treatments or vaccines against MERS-CoV. Thus, rapid laboratory identification of the infected animals and humans and contact tracing is critical in controlling spread of the infection.

RT-RCR is the current method of choice for the diagnosis of MERS-CoV and has high sensitivity and specificity; however, nucleic acid-based tests require molecular skills and specialized equipment making them unsuitable as point-of-care testing (POCT) or for rapid bedside diagnosis.

An alternative to RT-RCR is antigen- or antibody-based immunodiagnostic testing. However, existing immunodiagnostic tests for MERS-CoV have a number of limitations.

Antibodies to MERS-CoV usually require immunization of mammals to produce either monoclonal or polyclonal antibodies, followed by repeated invasive blood collection from the immunized mammal, and subsequent euthanasia of the mammal.

For human immunodiagnostics, mammalian antibodies often cross-react or are subject to interference by other mammalian proteins contained in a diagnostic sample. For example, mammalian antibodies can react with rheumatoid factor (RF), mammalian complement components, or mammalian Fc receptors. Moreover, monoclonal antibodies which are typically produced in mice can interact with human anti-mouse IgG antibodies (HAMA). These interactions make immunodiagnostic testing less accurate due to false positive results caused by these interactions.

Immunodiagnostic tests which use antibodies that recognize MERS-CoV S protein (a surface exposed antigen) can lack specificity due to variation of the amino acid sequences of S proteins. Such variation leads to S proteins from different strains of MERS-CoV presenting different epitopes. This can produce false negative results or lower sensitivity because antibodies to S protein from one strain of MERS-CoV may not recognize S protein epitopes from a different strain or only recognize a subset of such epitopes leading to lower sensitivity.

Moreover, the immunological repertoires of mammals may not produce antibodies that recognize important epitopes of MERS-CoV, for example, segments of N protein that resemble conserved mammalian (or "self") proteins may not be recognized by the mammalian immune system. Additionally, mammalian antibody repertoires may constitute too few sub-types to recognize certain diagnostic or therapeutic epitopes of MERS-CoV or may contain antigen processing and presentation systems that fail to present certain MERS-CoV epitopes.

In view of these challenges to existing detection methods, the inventors sought to develop highly specific, sensitive, economical, rapid, and user friendly methods for detection of MERS-CoV for use in the diagnostic laboratory as well as in the field or at the bedside.

The inventors considered that differences in genetic background and phylogenetic distance between avians and mammals as well as in differences in coronavirus tropism might be reflected by better or broader IgY antibody responses to MERs-CoV N protein in comparison to antibody responses produced by mammals. Such a broader or better response may be reflected by differences in the numbers of N protein epitopes recognized by avian IgY or by higher binding affinity of IgY antibodies to particular epitopes of N protein.

The inventors also recognized that immunoassays that use homologous mammalian antibodies may negatively impact assay performance by producing false negative or false positive readings. For example, immunoassays using mammalian immunoglobulins as bioactive molecules to capture or detect the analyte are affected by heterophilic antibodies and/or high levels of non-specific antibody binding. As mentioned above, nonspecific binding can occur between mammalian anti-MERS-CoV antibodies and other components of the mammalian immune system or hematological system. For example, mammalian antibodies specific for MERS-CoV can with rheumatoid factor (RF), complement components or mammalian Fc receptors, thus producing false-positive results. False positives may also result from the presence of heterophilic human antibodies, or human antibodies that bind to animal antibodies used in an immunochemistry assay, such as murine antibodies. False negative readings can be produced by failure of an antibody to recognize epitopes of an analyte (like a MERS-CoV antigen) or lack of sufficient binding affinity for epitopes of the analyte; or by interference by serum proteins with recognition of the analyte by an analyte-specific antibody.

BRIEF SUMMARY OF THE INVENTION

In view of these problems, the inventors sought to determine whether IgY antibodies from chickens, either as polyclonal or monoclonal preparations, might offer recognizable advantages over their mammalian homologues for immunodiagnosis of MERS-CoV. With these potential advantages in mind, the inventors sought to investigate, develop and characterize IgY antibodies to MERS-CoV N protein which could provide a broader or different ability to recognize MERS-CoV epitopes than their mammalian homologues. They also sought to identify IgY antibodies having a higher binding affinity or avidity for MERS-CoV N protein than mammalian homologues of IgY like IgG or IgE antibodies.

Embodiments of the invention include, but are not limited to the following.

One embodiment of this technology is an assay for detecting MERS-CoV in a sample comprising contacting the sample with an IgY antibody that recognizes MERS-CoV N protein ("NP") and detecting complex formation or binding of the IgY to the MERS-CoV. Preferably, the IgY antibody that recognizes N protein is a polyclonal antibody or a polyclonal monospecific antibody to a particular epitope or segment of N protein, for example, a peptide segment or fragment of the N protein sequence that comprises at least 4, 5, 6, 7, 8, 9, 10, 11, 12, 13, 14, 15, 16, 17, 18, 19, 20 or >20 contiguous amino acid residues. In other embodiments, the monospecific antibody may specifically bind to longer segments of N protein such as to the N or C domains of N protein. In other embodiments, the IgY antibody may be monoclonal antibody or mixture of 2, 3, 4, 5, 6 or more monoclonal antibodies that bind to N protein. It may also be polyclonal serum derived from an immunized chicken or other avian that has not been further purified to remove antibodies that do not bind to N protein.

This assay may be a direct or indirect ELISA assay, such as an ELISA sandwich assay, wherein the IgY antibody that recognizes MERS-CoV NP is a capturing antibody bound to a substrate, wherein the capturing antibody bound to the substrate is contacted with a sample suspected of containing MERS-CoV, and wherein complex formation is measured by the binding of a tagged secondary antibody that recognizes MERS-CoV.

It may also constitute an immunoswab assay, which comprises contacting a sample with IgY antibodies bound to a swab (such as a swab comprising calcium alginate), removing unbound sample, and detecting complex formation. Swabs suitable for use as immunoswabs are commercially available.

The IgY-based assays disclosed herein may detect N protein in a biological sample containing no more than 10, 15, 20, 25, 30, 35, 40, 45 or 50 ng/ml of N protein.

Preferably, the IgY antibody does not substantially interact with rheumatoid factor (RF), human anti-mouse IgG antibodies (HAMA), or other heterophilic antibodies, mammalian complement components or other serological proteins, and/or mammalian Fc receptors.

In the assays disclosed herein the IgY antibody is a polyclonal antibody, monospecific antibody which may be polyclonal, or monoclonal antibody. In some embodiments, the polyclonal antibody is produced by immunizing chickens with isolated or recombinant NP and recovering IgY antibody from eggs laid by the immunized chickens.

Monospecific antibodies to particular determinants or epitopes of N protein may be isolated by affinity purification using such N protein determinants. Monospecific antibodies may also be obtained by immunizing a chicken or other avian with a particular peptide fragment of N protein, for example, a chicken may be immunized with the N or C domain of N protein so that only antibodies to the N or C domain are induced.

In some embodiments of the assay, the IgY antibody binds to at least one epitope within the amino acid sequence described by SEQ ID NO: 1 or an N protein analog having at least 95, 96, 97, 98, 99, 99.5, 99.9% or more similarity or identity thereto or to an N protein having up to 1, 2, 3, 4, 5, 6, 7, 8, 9, 10, 11, 12, 13, 14, 15, 16, 17, 18, 19, 20, 21, 23, 24, or 25 amino acid insertions, substitutions and/or deletions to SEQ ID NO: 1. A nucleoprotein comprising SEQ ID NO: 1 is available from Sino Biological and was used for development of the monospecific anti-NP IgY antibodies disclosed herein. This NP sequence and associated structural or functional features are incorporated by reference to GenBank: AFS88943.1.

BLASTP can be used to identify an amino acid sequence having at least 70%, 75%, 80%, 85%, 87.5%, 90%, 92.5%, 95%, 97.5%, 98%, 99%, 99.5%, or >99.5% sequence identity or similarity to a reference amino acid using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting uses an Expect Threshold of 10, a Word Size of 3, BLOSUM 62 as a matrix, and Gap Penalty of 11 (Existence) and 1 (Extension) and a conditional compositional score matrix adjustment. Default settings for BLASTP are described by and incorporated by reference to hypertext transfer protocol://blast.ncbi.nlm.nih.gov/Blast.cgi?PROGRAM=blastp&PAGE_TYPE=BlastSearch&LINK_LOC=blasthome (last accessed Oct. 2, 2020).

In one embodiment, the IgY antibody comprises a monospecific antibody that binds to a peptide epitope of N protein that ranges in length from 6, 7, 8, 9, 10, 11, 12, 13, 14, 15, 16, 17, 18, 19 to 20 amino acids of the amino acid sequence described by SEQ ID NO: 1 or an analog thereof.

In another embodiment, the IgY antibody comprises a monospecific antibody that binds to an N-terminal domain segment comprising residues 1-36 of SEQ ID NO: 1.

In another embodiment, the IgY antibody comprises a monospecific antibody that binds to an N-terminal domain of MERS CoV N protein comprising residues 37-164 of SEQ ID NO: 1.

In another embodiment the IgY antibody comprises a monospecific antibody that binds to a central segment of MERS CoV N protein comprising residues 165-238 of SEQ ID NO: 1; or that binds to a disordered region or LKR containing a stretch of serine and arginine residues and comprising residues 156 to 206 of SEQ ID NO: 1 or LPKNFHIEGTGGNSQSSSRASSVSRN-SSRSSSQGSRSGNSTRGTSPGPSGI (SEQ ID NO: 3).

In another embodiment, the IgY antibody comprises a monospecific antibody that binds to a C-terminal domain of MERS CoV N protein comprising residues 239-362 of SEQ ID NO: 1.

In another embodiment, the IgY antibody comprises a monospecific antibody that binds to a C-terminal segment of MERS CoV N protein comprising residues 363-413 of SEQ ID NO: 1.

In some embodiments, the IgY antibody comprises a monospecific antibody that binds to a peptide comprising positions 4-12, 42-47, 50-58, 60-66, 92-102, 108-126, 144-150, 172-180, 206-225, 230-240, 261-268, 296-304, 324-337, 347-353 or 399-405 described by SEQ ID NO: 1. These segments of N protein have been identified using bioinformatics as B cell epitopes. These and the description of humoral and cellular epitopes and determinants of N protein and bioinformatic methods for identifying them are incorporated by reference to Jiandong Shi, et al. *Epitope-Based Vaccine Target Screening against Highly Pathogenic MERS-CoV: An In Silico Approach Applied to Emerging Infectious Diseases*, PLOS ONE, December 2015, hypertext transfer protocol secure://doi.org/10.1371/journal.pone.0144475. The corresponding epitopes and N protein sequences as given by the above reference are also incorporated by reference.

In an alternative embodiment, any of the B cell epitopes herein may be modified by 1 or 2 deletions, substitutions, or insertions of an amino acid. Such epitopes may also be conjugated to other moieties or embedded in a longer endogenous or exogenous carrier protein to improve their immunogenicity or their ability to bind to IgY antibodies.

In other embodiments, the IgY antibody comprises a monospecific antibody that binds to a peptide segment consisting of the following residues of a polypeptide comprising SEQ ID NO: 1:

K346, W347, L348, and E349;
Y327, F328, L329, and R330;
L350, L351, E352, O353, N354, I355, D356, A357, Y358, K359, T360, F361, P362, 1063 1064, and E365;
D320, D321, H322, G323, N324, P325, and V326;
H252, K253, R254, T255, S256, T257, K258, S259, F260, N261, M262, V263, Q264, A265, F266, G267, L268, R269, G270, P271, G272, D273, L274, Q275, G276, N277, F278, G279, D280, L281, Q282, L283, N284, K285, L286, G287, T288, E289, D290, P291, and R292;
R399, P400, S401, V402, Q403, P404, G405, P406, M407, I408 D409, V410, N411, T412, and D413;
W293, P294, 0295, 1296, A297, and E298;
F312, K313, L314, T315, H316, Q317, N318, and N319; and
L299, A300, P301, T302, A303, S304, A305, F306, M307, G308, M309, 5310, and Q311.

The corresponding epitopes and N protein sequences as described by Shi et al., supra are also incorporated by reference.

IgY antibodies that bind to one of the above combinations of N protein residues may be characterized as antibodies that recognize conformational epitopes; see Jiandong Shi, et al., supra.

The invention also pertains to a diagnostic method using a mixture of two, three, four or more monospecific antibodies recognizing different epitopes or domains of the N protein.

Another aspect of this technology is directed to an antibody conjugate comprising any of the antibodies disclosed herein including to a monospecific polyclonal IgY antibody that binds to the N terminal domain of MERS-CoV that is conjugated to at least one detectable marker or to a therapeutic agent; or to an antibody conjugate comprising a monospecific polyclonal IgY antibody that binds to the LKR of MERS-CoV that is conjugated to at least one detectable marker or to a therapeutic agent; and/or to an antibody conjugate comprising a monospecific polyclonal IgY antibody that binds to the C terminal domain of MERS-CoV that are conjugated to at least one detectable marker or to a therapeutic agent. The IgY antibodies, or their antigen binding fragments and conjugates may also be attached to a solid substrate such as a microtiter plate well or to chromatography beads or other substrates such as woven or non-woven materials or to a plastic, metal, silicon, or glass surface.

Another aspect of this technology is a method for treating a subject at risk of being infected by, or infected by, MERS-CoV comprising administering an IgY antibody, chimeric IgY antibody or humanized IgY antibody to the subject. In one embodiment, the method comprises administering an IgY composition or pharmaceutical composition intravenously, intramuscularly, topically, intradermally, intramucosally, subcutaneously, sublingually, orally, intravaginally, intracavernously, intraocularly, intranasally, intrarectally, gastrointestinally, intraductally, intrathecally, subdurally, extradurally, intraventricular, intrapulmonary, into an abscess, intra articularly, into a bursa, subpericardially, into an axilla, intrauterine, into the pleural space, intraperitoneally, transmucosally, or transdermally. Advantageously, a humanized IgY composition typically comprising one or more humanized monoclonal antibodies, such as an IgG antibody having its CDRs replaced with IgY CDRs, or an IgY antibody having its non-CDR regions replaced by IgG regions, may be administered into the nasal cavity, sinuses, or upper or lower respiratory system.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

FIG. 3. Illustration of some steps of production and purification of IgY antibodies in avians and use of IgY antibodies in antibody-based assay for MERS-CoV N protein.

DETAILED DESCRIPTION OF THE INVENTION

Figure 1:
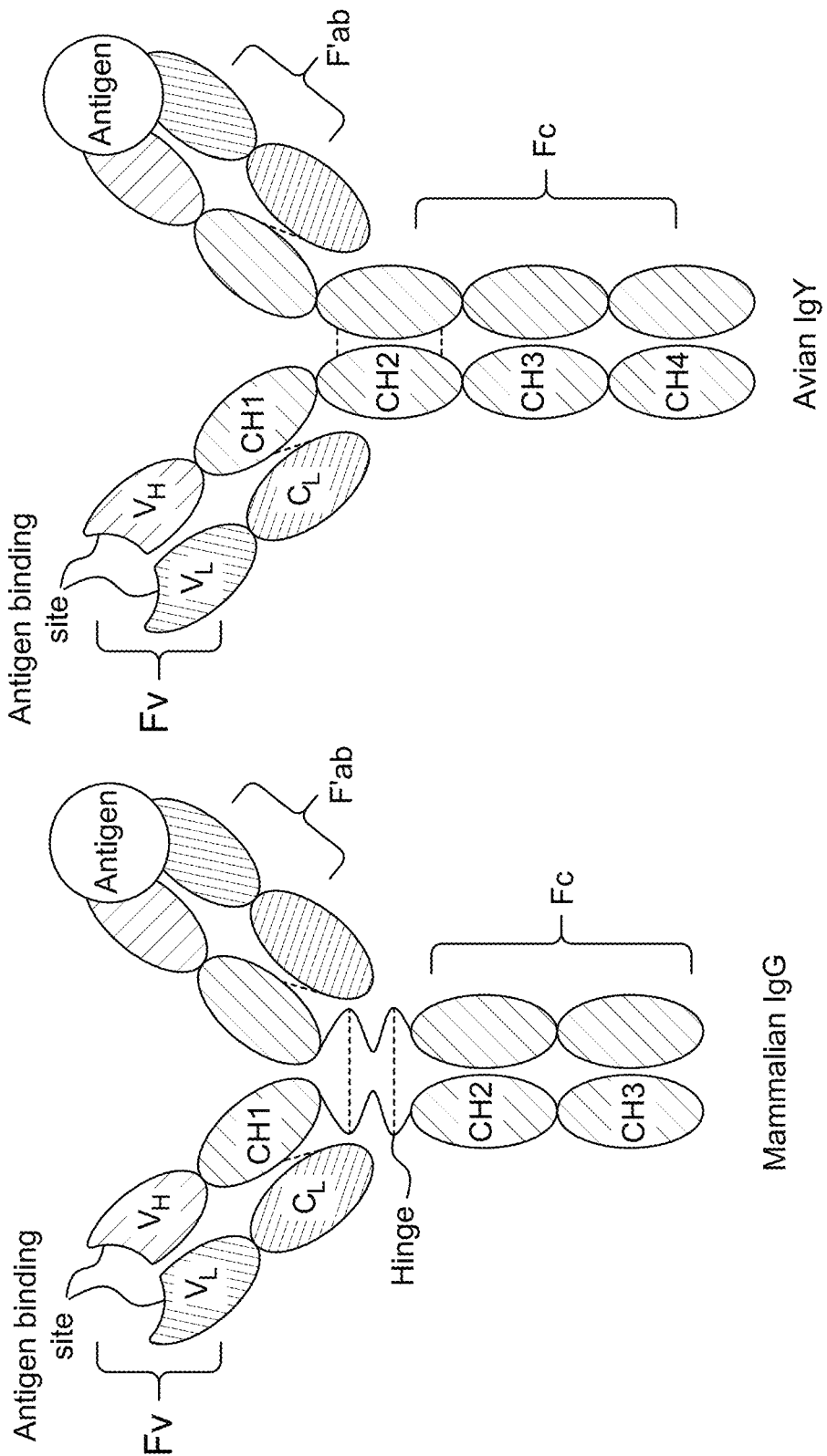
FIG. 1. Comparison of IgY and IgG structures.
Figure 2:
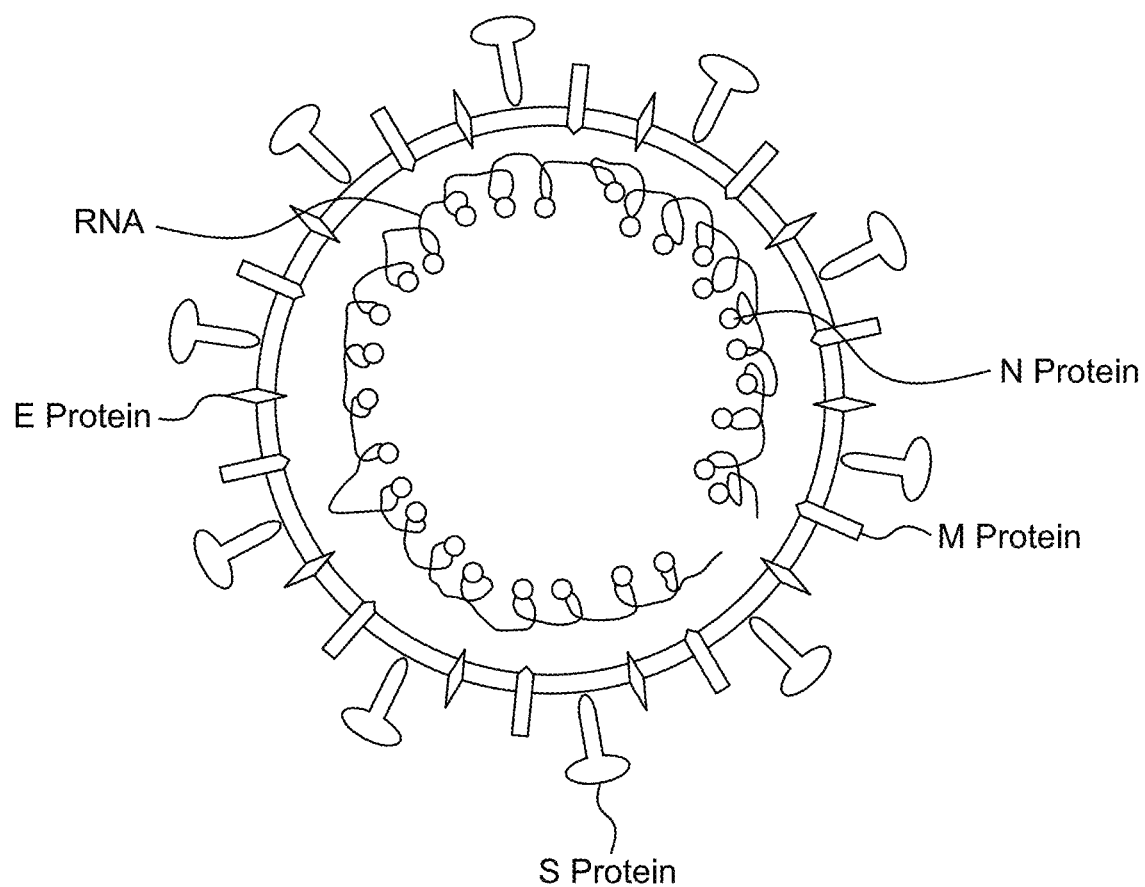
FIG. 2. Components of MERS-CoV.
Figure 4:
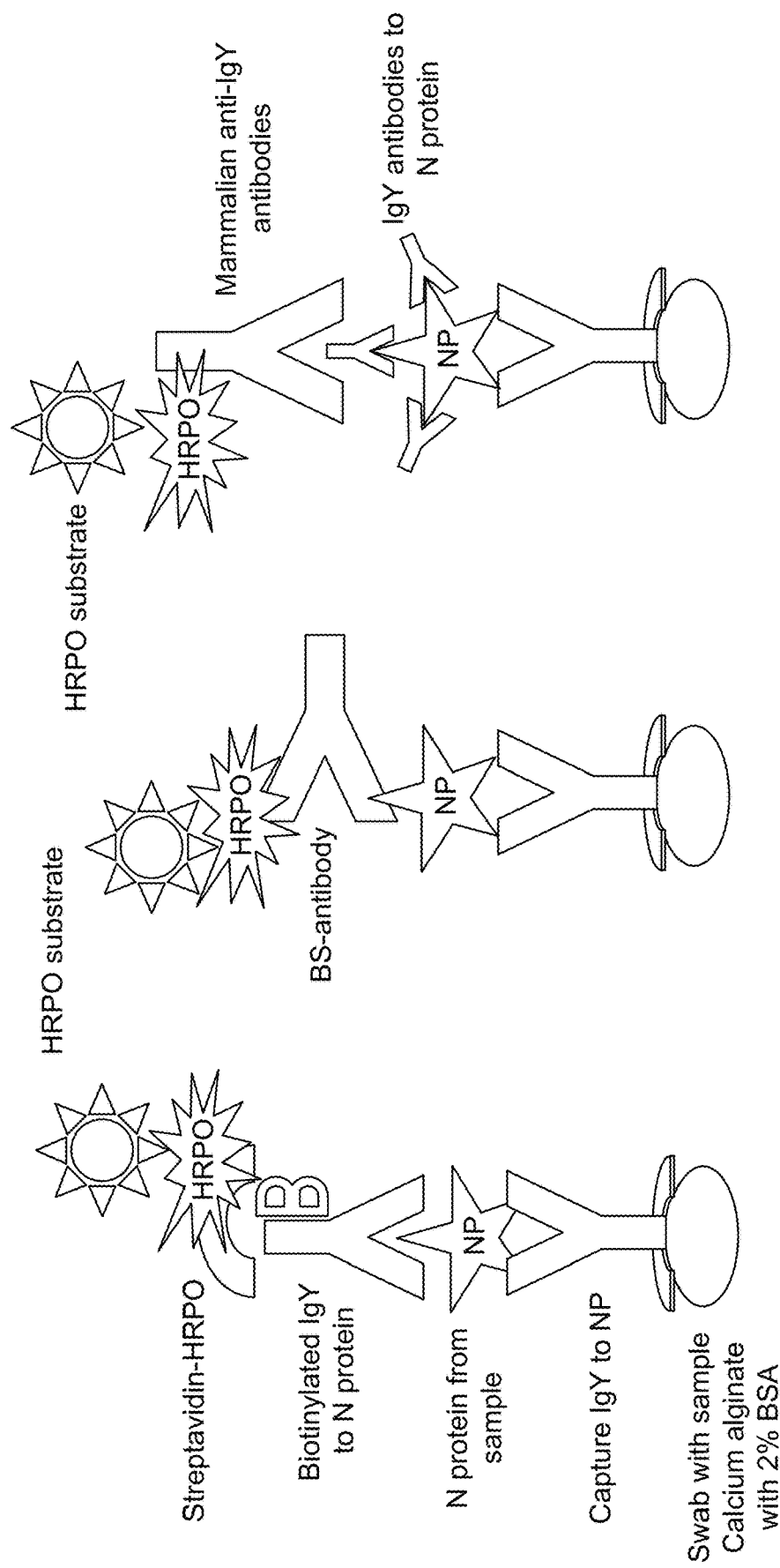
FIG. 4. Illustration of one embodiment of an immunoswab assay for N protein.

The enzyme-linked immunosorbent assay (ELISA) is a commonly used analytical biochemistry assay. The assay uses a solid-phase type of enzyme immunoassay (EIA) to detect the presence of a ligand in a liquid sample using antibodies directed against the ligand to be measured. In the present invention, an IgY-based ELISA is used to detect a protein ligand, MERS-CoV N protein.

In one simple form of an ELISA, a sample to be tested for a particular antigen such as MERS-CoV N protein is attached to a surface such as to the bottom of a microtiter plate well. An antigen-specific IgY antibody, which has been linked to an enzyme, is applied over the surface so it can bind the antigen. Unbound IgY antibodies are removed. In the final step, a substance containing the enzyme's substrate is added. If there is binding between the MERS-CoV N protein and the IgY antibody the subsequent reaction produces a detectable signal, most commonly a color change.

Performing an ELISA involves at least one IgY antibody with specificity for MERS-CoV N protein antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized, an antigen-specific detection antibody is added, forming a complex with the antigen. The detection antibody can be covalently linked to an enzyme or can itself be detected by a secondary antibody that is linked to an enzyme through bioconjugation. Between each step, the plate is typically washed with a mild detergent solution to remove any proteins or antibodies that are non-specifically bound. After the final wash step, the plate is developed by adding an enzymatic substrate to produce a visible signal, which indicates the quantity of antigen in the sample.

Diagnostic samples for ELISA may be obtained from subjects exposed to or infected with MERS-CoV. Subjects include humans such as a male or female child less than reproductive age, a male or female of reproductive age, a pregnant female, or an adult. The subject may be one at risk of exposure to MERS-CoV such as one who works in proximity to infected humans or animals or who is exposed to animal products like milk or meat, animal fluids such as saliva or blood, or animal waste products such as urine or feces, or a human or animal otherwise at risk of, or that is, infected with MERS-CoV.

Samples may also be acquired from subjects with impaired respiratory systems including pneumonia, cystic fibrosis, tuberculosis, asthma, emphysema, bronchitis, smokers, lung cancer, pneumoconiosis, and chronic bronchitis and other forms of COPD, autoimmune diseases, or from those at risk of immune dysfunction or immunodeficiency. In some preferred embodiments, a sample is collected by nasopharyngeal swab, nasopharyngeal aspirate, nasal wash, or nasopharyngeal wash.

Subjects for diagnosis. A subject from whom a biological sample is taken for diagnostic testing may be a human or be a non-human animal such as a member of the Camelidae family, such as a dromedary or a Bactrian camel or a llama, alpaca, vicuña, or guanaco. A subject may also be a pet (e.g., dog or cat), livestock (e.g., horse, cattle, goats, sheep, pigs) or wild animal (e.g., bats, mice, rats) susceptible to infection with MERS-CoV or which act as a vectors, carriers or reservoirs for the virus. The term subject includes both adult and juvenile and male and female subjects.

In addition to the human an animal subjects mentioned above from whom samples may be taken, subjects at risk of an active vaccine-induced lung pathology may be selected for passive immunization to avoid the side-effects of administering an immunogenic viral protein.

The method as disclosed herein may be used with antibody (IgY) based assays. Some preferred types of assays include ELISA (indirect or direct competitive ELISA sandwich ELISA, direct or indirect ELISA), immunodiffusion, immunochromatography assay, western blotting, and immunohistochemistry assay including immunofluorescence.

Additional types or details of ELISA assays for use with IgY as disclosed herein are described below.

Direct ELISA. The steps of direct ELISA substantially follow the mechanism below: A buffered solution of the antigen to be tested for is added to each well (usually 96-well plates) of a microtiter plate, where it is given time to adhere to the plastic through charge interactions. A solution of nonreacting protein, such as bovine serum albumin or casein, is added to each well in order to cover any plastic surface in the well which remains uncoated by the antigen. The primary antibody with an attached (conjugated) enzyme is added, which binds specifically to the test antigen coating the well. A substrate for this enzyme is then added. Often, this substrate changes color upon reaction with the enzyme. The higher the concentration of the primary antibody present in the serum, the stronger the color change. Often, a spectrometer is used to give quantitative values for color strength.

The enzyme acts as an amplifier; even if only few enzyme-linked antibodies remain bound, the enzyme molecules will produce many signal molecules. Within common-sense limitations, the enzyme can go on producing color indefinitely, but the more antibody is bound, the faster the color will develop. A major disadvantage of the direct ELISA is that the method of antigen immobilization is not specific; when serum is used as the source of test antigen, all proteins in the sample may stick to the microtiter plate well, so small concentrations of analyte in serum must compete with other serum proteins when binding to the well surface. The sandwich or indirect ELISA provides a solution to this problem, by using a "capture" antibody specific for the test antigen to pull it out of the serum's molecular mixture ELISA may be run in a qualitative or quantitative format. Qualitative results provide a simple positive or negative result (yes or no) for a sample. The cutoff between positive and negative is determined by the analyst and may be statistical. Two or three times the standard deviation (error inherent in a test) is often used to distinguish positive from negative samples. In quantitative ELISA, the optical density (OD) of the sample is compared to a standard curve, which is typically a serial dilution of a known-concentration solution of the target molecule. For example, if a test sample returns an OD of 1.0, the point on the standard curve that gave OD=1.0 must be of the same analyte concentration as the sample.

The use and meaning of the names "indirect ELISA" and "direct ELISA" differs in the literature and on web sites depending on the context of the experiment. When the presence of an antigen is analyzed, the name "direct ELISA" refers to an ELISA in which only a labelled primary antibody is used, and the term "indirect ELISA" refers to an ELISA in which the antigen is bound by the primary antibody which then is detected by a labeled secondary antibody. In the latter case a sandwich ELISA is clearly distinct from an indirect ELISA. When the "primary" antibody is of interest, e.g. in the case of immunization analyses, this antibody is directly detected by the secondary antibody and the term "indirect ELISA" applies to a setting with two antibodies.

Sandwich ELISA. A plate is coated with a capture antibody; a sample is added, and any antigen present binds to capture antibody; a detecting antibody is added, and binds to antigen; an enzyme-linked secondary antibody is added, and binds to detecting antibody then substrate is added, and is converted by enzyme to detectable form. A "sandwich" ELISA is used to detect sample antigen. The steps are: A surface is prepared to which a known quantity of capture antibody is bound. Any nonspecific binding sites on the surface are blocked. The antigen-containing sample is applied to the plate, and captured by antibody. The plate is washed to remove unbound antigen. A specific antibody is added, and binds to antigen (hence the 'sandwich': the antigen is stuck between two antibodies). This primary antibody could also be in the serum of a donor to be tested for reactivity towards the antigen. Enzyme-linked secondary antibodies are applied as detection antibodies that also bind specifically to the antibody's Fc region (nonspecific). The plate is washed to remove the unbound antibody-enzyme conjugates. A chemical is added to be converted by the enzyme into a color or fluorescent or electrochemical signal. The absorbance or fluorescence or electrochemical signal (e.g., current) of the plate wells is measured to determine the presence and quantity of antigen. Without the first layer of "capture" antibody, any proteins in the sample (including serum proteins) may competitively adsorb to the plate surface, lowering the quantity of antigen immobilized. Use of the purified specific antibody to attach the antigen to the plastic eliminates a need to purify the antigen from complicated mixtures before the measurement, simplifying the assay, and increasing the specificity and the sensitivity of the assay. A sandwich ELISA used for research often needs validation because of the risk of false positive results.

Competitive ELISA. Another use of ELISA is through competitive binding. The steps for this ELISA are somewhat different from the first two examples: unlabeled antibody is incubated in the presence of its antigen (sample). These bound antibody/antigen complexes are then added to an antigen-coated well. The plate is washed, so unbound antibodies are removed. (The more antigen in the sample, the more Ag-Ab complexes are formed and so there are less unbound antibodies available to bind to the antigen in the well, hence "competition".) The secondary antibody, specific to the primary antibody, is added. This second antibody is coupled to the enzyme. A substrate is added, and remaining enzymes elicit a chromogenic or fluorescent signal. The reaction is stopped to prevent eventual saturation of the signal. Some competitive ELISA kits include enzyme-linked antigen rather than enzyme-linked antibody. The labeled antigen competes for primary antibody binding sites with the sample antigen (unlabeled). The less antigen in the sample, the more labeled antigen is retained in the well and the stronger the signal. Commonly, the antigen is not first positioned in the well.

Figure 3:
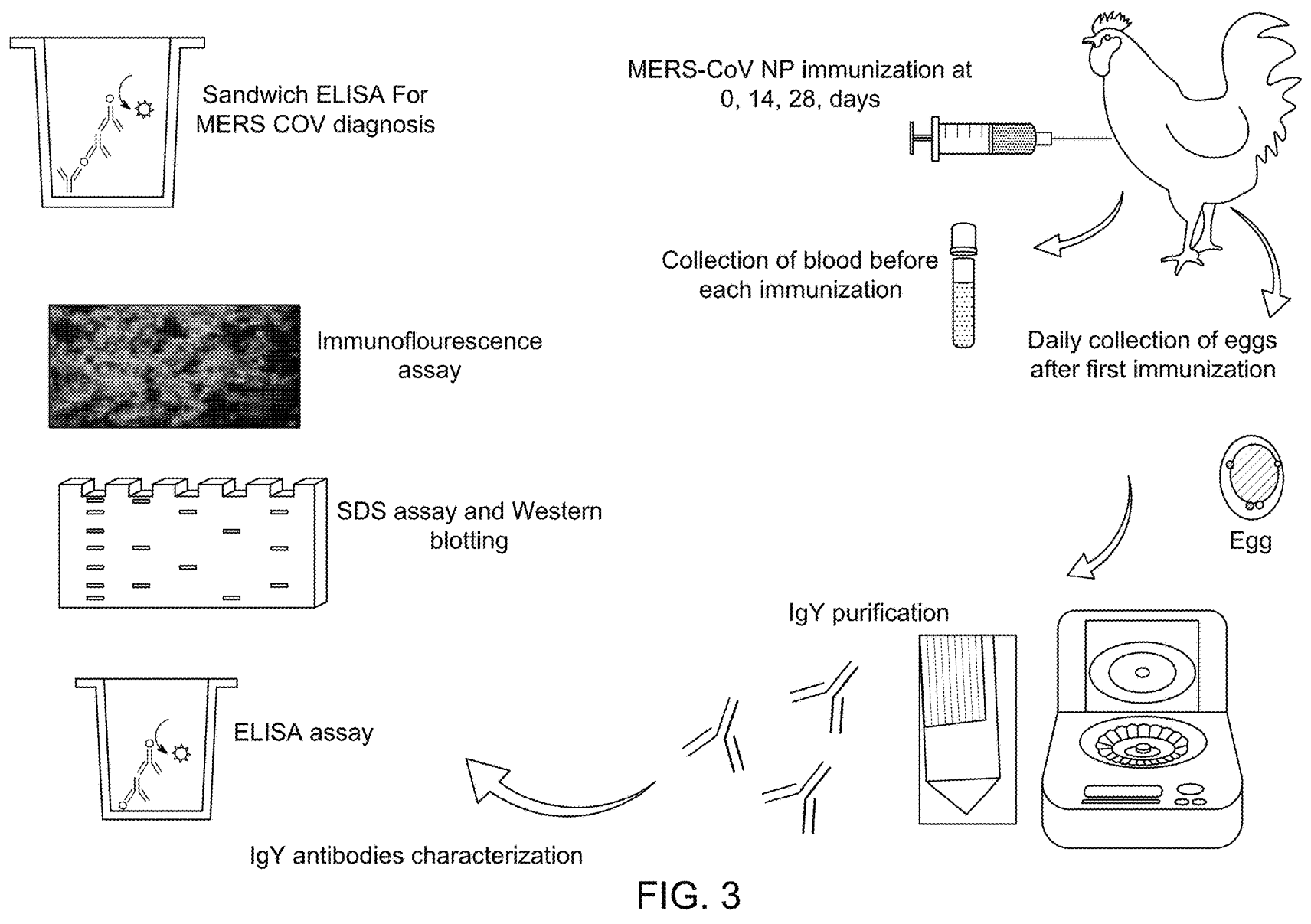

Immunoswab. One embodiment of this assay is incorporated by reference to Kammila, S, et al. *A rapid point of care immunoswab assay for SARS-CoV detection*." JOURNAL OF VIROLOGICAL METHODS, 2008, 152(1-2): 77-84. This assay may be performed with the IgY antibodies disclosed herein. FIG. 3 describes several variants of this method. Briefly, a capture antibody that recognizes MERS-CoV N protein is bound to a swab, such as a calcium alginate swab, unbound antibody is rinsed off, unbound sites are quenched with 2% BSA or other protein. For detection of N protein, a biological sample suspected to containing N protein is applied to the swab. Unbound material is washed off and an enzyme-linked detecting antibody which binds to N protein is applied. Unbound antibody is washed off and binding or the amount of binding is detected by action of an enzyme bound to the detecting antibody on a substrate. Preferably, both the capture and detecting antibodies are IgY, which may be monoclonal, monospecific, or polyspecific IgY. In some embodiments, the detecting antibody comprises biotin and the enzyme comprises strepavidin and horseradish peroxidase and the substrate for the enzyme is 3,3',5,5'-Tetramethylbenzidine or TMB. A similar system has been used to detect SARS N protein. In view of the structural and immunological differences among various Coronavirus N proteins, one objective was to determine whether this system would provide high specificity and sensitivity for detection of MERS-CoV N protein and which IgY antibodies should be selected for such an assay.

One skilled in the art can select an appropriate enzymatic marker for ELISA. Enzymatic markers for ELISA include OPD (o-phenylenediamine dihydrochloride) turns amber to detect HRP (Horseradish Peroxidase), which is often used to as a conjugated protein. TMB (3,3',5,5'-tetramethylbenzidine) turns blue when detecting HRP and turns yellow after the addition of sulfuric or phosphoric acid. ABTS (2,2'-Azinobis [3-ethylbenzothiazoline-6-sulfonic acid]-diammonium salt) turns green when detecting HRP. PNPP (p-Nitrophenyl Phosphate, Disodium Salt) turns yellow when detecting alkaline phosphatase.

MERS-CoV neutralization assay may be performed using the IgY antibody products disclosed herein. Such assays are known in the art and can be adapted to use of IgY antibodies that recognize MERS-CoV N protein or its epitopes. Such assays are also incorporated by reference to Amanat, F., et al., *An in vitro microneutralization assay for SARS-CoV-2 serology and drug screening*, CURRENT PROTOCOLS, 2020, 58(1). Such assays may be used to detect levels of neutralizing antibodies in a sample, identify neutralizing epitopes on N protein, or identify CDRs useful for making chimeric or humanized antibodies.

Other tests and assays for detection of MERS-CoV or MERS-CoV N protein with IgY. These include immunochromatographic, western blotting, immunoenzymatic, immunofluorescence tests or tests performed using immunosensors.

In addition to the immunodiagnostic methods disclosed herein, the IgY antibody products disclosed herein may be used as immunotherapeutics.

Nucleocapsid or N protein. The N protein of MERS-CoV is a phosphorylated basic protein and is the second largest structural protein, containing 413 amino acid residues. The N protein binds to the RNA genome to form a nucleocapsid, which is important for virus replication. The NP is the most abundantly expressed antigen among the other MERS-CoV antigens and amino-acid mutations are uncommon. SEQ ID NO: 1 describes an MERS-CoV N protein sequence and SEQ ID NOS: 2 and 3 segments of the N protein. MERS-CoV N protein functions as an IFN antagonist. It suppresses RIG-I-induced type I and type III IFN production by interfering with TRIM25-mediated RIG-I ubiquitination. Antibodies against the N protein may appear before antibodies against the S protein. Thus, the inventors believe that sensitive detection of N protein in bodily fluids is important for diagnosis or for assessing host response to viral infection. Other structural and functional features of MERS-CoV N protein are incorporated by reference to Li, Y. et al., *Molecular Characteristics, Functions, and Related Pathogenicity of MERS-CoV Proteins*, ENGINEERING, 2019, 5(5), 940-947.

IgY. In chickens, immunoglobulin Y is often compared to Immunoglobulin G (IgG). Like IgG, it is composed of two light and two heavy, but has a shorter heavy chain the IgG. The steric flexibility of the IgY molecule is less than that of IgG.

IgY passes from an immunized hen's blood to her eggs and extraction of the IgY from egg yolks provides simple and non-invasive alternative for antibody production. Production of IgY in high yields compared to production of IgG antibodies in mammals, such as rabbits provides an advantage. One chicken can produce about 22 gr of IgY antibodies with 2-10% of the antibodies being target (immunogen) specific. This exceeds the production of IgG from four rabbits. IgY antibodies can be stored in eggs at 4° C. for at least one year.

IgYs generally have no interactions with mammalian immune components or assay materials used to detect mammalian antibodies. These include non-reactivity with cellular Fc receptors, mammalian IgG, rheumatoid factor, mammalian complement components, protein A, and protein G. This lack of reactivity helps reduce the occurrence of false positive results in assays employing IgY instead of IgG.

In addition, the avian IgY repertoire differs from mammalian repertoire permitting IgY to bind to epitopes not recognized, or poorly recognized by mammalian antibodies.

IgY antibodies may have $K_D$ or average $K_D$ values ranging from micomolar ($10^{-6}$ L/mol), to nanomolar ($10^{-7}$-$10^{-9}$ L/mol). High affinity IgY antibodies may have $K_D$s in the picomolar range up to $10^{-12}$ L/mol. Binding affinity is typically measured and reported by the equilibrium dissociation constant ($K_D$), which is used to evaluate and rank order strengths of bimolecular interactions. In biochemistry or pharmacology, protein-ligand complex having high affinity if the Kd is below 100 nM (for antibody-antigen complex below 10 nM), medium affinity in the range 100 nM-10 uM, and low affinity if the Kd is above 10 uM. IgY antibodies as disclosed herein may have $K_D$ values in the low micromolar (about $10^{-6}$) to nanomolar (about $10^{-7}$, $10^{-8}$ to $10^{-9}$) range or in the low nanomolar range of about $10^{-9}$, $10^{-10}$ or $10^{-11}$ with very high affinity antibodies being in the picomolar ($10^{-12}$) range.

In some embodiments chicken IgY exhibits high avidity of about $10^{-9}$ L/mol. Avidity is the strength of interaction between a multivalent antibody and epitopes.

The inventors considered that chicken IgY polyclonal antibodies would have higher avidity, higher specificity and lower cross-reactivity as compared to IgG antibodies, that they could have a broader antigen-binding host range, due to the great evolutionary distance between chickens and mammals, and that they could exhibit high avidity ($10^{-9}$ L/mol) even after the first immunization. Moreover, the inventors considered that the response of immunoglobulins in chickens to the highly conserved mammalian proteins would be robust showing higher affinity, thereby potentially targeting broad spectrum of epitopes on protein immunogens.

In some embodiments, monospecific IgY antibodies are eluted from an affinity column and purified away from other antibodies and components. Affinity chromatography is a method used for purification of a specific molecule or group of molecules from a mixture. By using the relationship between two molecules, such as the affinity between an antigen and antibody, one can purify the desired biological molecules.

Most methods disclosed herein may employ naturally occurring IgY antibodies such as those produced by exposure or immunization of a chicken or other avian to MERS-CoV N protein or its epitopes. In some embodiments, these are isolated from the egg yolks of immunized avians. These are typically polyclonal antibodies, however antigenic specificity of the polyclonal antibodies may be tailored by choice of immunization with the entire N protein, denatured or soluble N protein, N protein quaternary forms (e.g., dimers or tetramers), or by immunization with N protein fragments or peptide epitopes. Alternatively, monoclonal MERS-CoV IgY antibodies may be used. These too may be directed to different linear or conformational epitopes of N protein.

Monospecific antibodies are antibodies whose specificity to antigens is singular in any of several ways: antibodies that all have affinity for the same antigen; antibodies that are specific to one antigen or one epitope; or antibodies specific to one type of cell or tissue. Monoclonal antibodies are monospecific, but monospecific antibodies may also be produced by other means than producing them from a common germ cell, for example, by immunization with a specific peptide epitope or other segment of a longer protein or by affinity purification to a substrate comprising an epitope of interest.

Immunization. Methods for immunizing an animal such as a chicken or other avian are known in the art and are incorporated by reference to LABORATORY TECHNIQUES IN BIOCHEMISTRY AND MOLECULAR BIOLOGY, 1966, 19, 131-144, see Chapter 4, *Immunization with peptides*. Preferably, the avians are inbred or genetically identical. In some methods adjuvants are used to boost production of IgY antibodies. An adjuvant is a pharmacological or agent that modifies the effect of other agents. Adjuvants may be added to a protein construct as disclosed herein, such as a conjugate comprising N protein epitopes and a carrier protein, to boost the humoral or cellular immune responses and produce more anti-IgY antibodies and longer-lasting immunity, thus minimizing the dose of protein construct needed. Adjuvants that may be compounded with, or otherwise used along with N protein, its fragments or peptide epitopes disclosed herein include, but are not limited to, inorganic compounds including alum, aluminum hydroxide, aluminum phosphate, calcium phosphate hydroxide; mineral oil or paraffin oil; bacterial products or their immunologically active fractions, such as those derived killed *Bordetella pertussis, Mycobacterium bovis*, or bacterial toxoids; organics such as squalene; detergents such as Quil A, saponins such as Quillaja, soybean or polygala senega; cytokines such as IL-1, IL-2 or IL-12; Freund's complete adjuvant or Freund's incomplete adjuvant; and food based oils like Adjuvant 65, which is a product based on peanut oil. Those skilled in the medical or immunological arts may select an appropriate adjuvant based on the type of patient and mode of administration of the protein construct of the invention.

Figure 5:
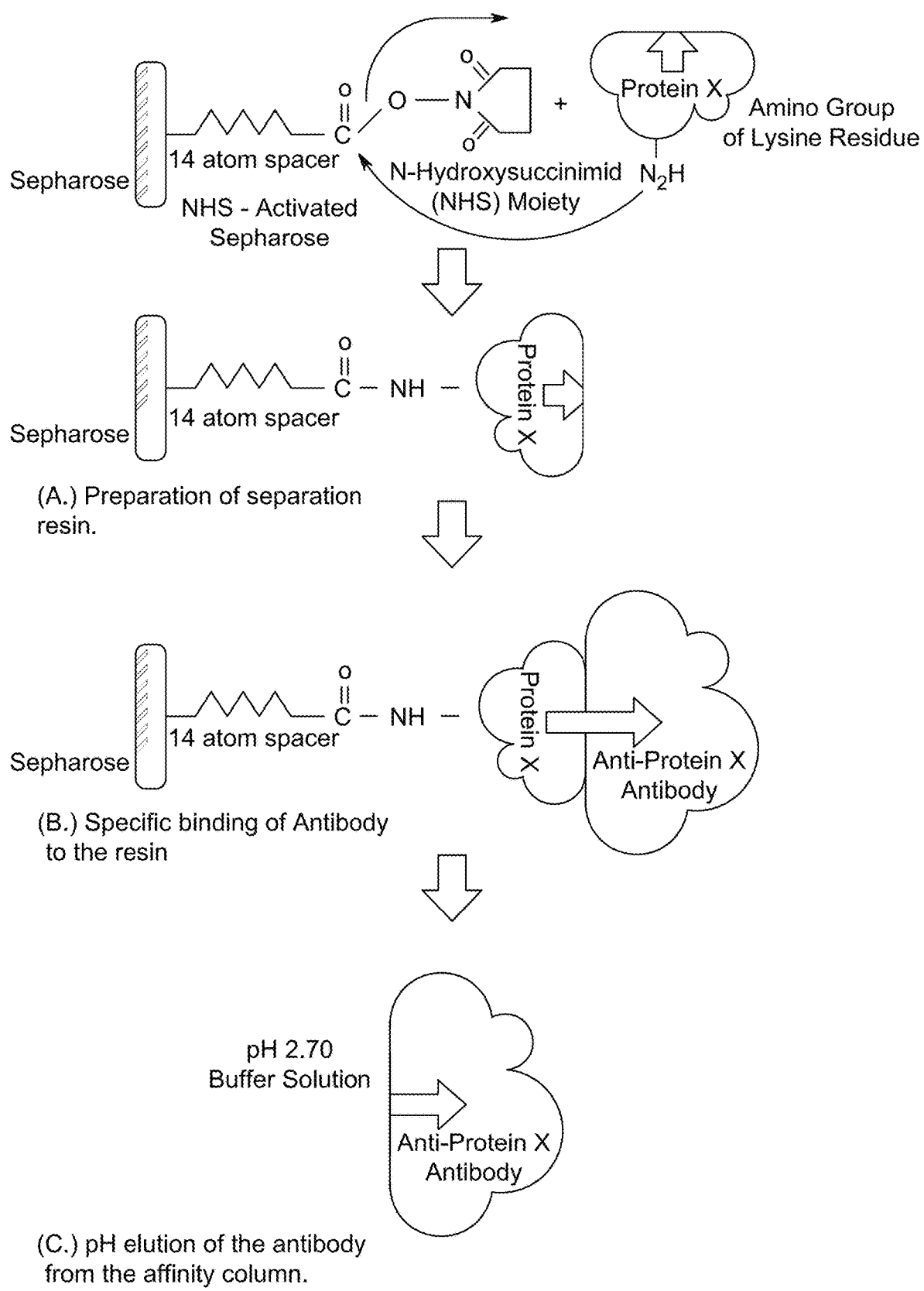
FIG. 5. Affinity purification of monospecific antibodies.

Affinity purification. IgY antibodies may be affinity purified to N protein, its fragments, or epitopes using methods known in the art. Such methods are also incorporated by reference to Hnasko, et al., *Affinity Purification of Antibodies*, METHODS MOL BIOL, 2015, 1318, 29-41 to Darcy, et al., Purification of Antibodies Using Affinity Chromatography, METHODS MOL BIOL., 2017; 1485, 305-318; or to Arora, et al., *Affinity chromatography br antibody purification*, METHODS MOL 2014; 1129:497-516. One example of affinity purification of antibodies is shown in FIG. 5.

Regarding antibodies, monospecific and monovalent overlap in meaning; both can indicate specificity to one antigen, one epitope, or one cell type (including one microorganism species). However, antibodies that are monospecific to a certain tissue, or all monospecific to the same tissue because clones, can be polyvalent in their epitope binding.

Monoclonal IgY antibodies to MERS-CoV N protein may be produced by methods known in the art or may be custom ordered to an antigen of interest commercially, for example, from Creative Biolabs, worldwide web.creative-biolabs.com/igy-antibody-generation.html (last accessed Oct. 2, 2020. One typical method for production of IgY monoclonal antibodies comprises PCR amplification of chicken genes encoding the IgY antibody repertoire followed by construction of a phage library. The phage library is then screened for positive antibody binders for N protein epitopes. Antibodies that bind to N protein are then expressed in *E. coli*, isolated and optionally further characterized as to affinity, avidity, stability and specificity. Monoclonal fragments, such as monoclonal scFv or Fab types of IgY antibody, may be produced in a similar manner after phage display library screening. Chimeric or humanized IgY may be produced by transferring the scFv regions of the IgY monoclonal antibodies into a human IgG expression vector and manufacturing the chimeric antibody in CHO cells.

Chicken antibody repertoires focused on a number of defined targets, such as MERS-CoV N protein or its epitopes, can be constructed using lymphocyte mRNA from chickens immunized with a single epitope or mixture of several different N protein epitopes. Immune responses to each of the individual epitopes can be determined by extracting egg-yolk IgY and testing for antigen-specific antibodies using ELISA. The chicken splenocytes are then recovered, RNA is extracted, and after reverse transcription, the immunoglobulin $V_H$ and $V_L$ regions are amplified by PCR and joined via a single glycyl residue for surface expression on a collection of filamentous bacteriophages. The resulting display library is screened by panning to isolate binders.

A "carrier" or "excipient", as used herein, includes any and all solvents, dispersion media, diluents, or other liquid vehicles, dispersion or suspension aids, surface active agents, isotonic agents, thickening or emulsifying agents, preservatives, solid binders, lubricants and the like useful for the diagnostic assays disclosed herein. This term also includes pharmaceutical carriers and excipients such as those described by and incorporated by reference to Remington's *The Science and Practice of Pharmacy*, 21st Edition, A. R. Gennaro, (Lippincott, Williams & Wilkins, Baltimore, Md., 2006). Any suitable buffer, carrier or excipient may be combined with the N protein-binding IgY, antigen-binding IgY portions. IgY CDRs, or IgY conjugates which bind to N protein; or with biological samples suspected of containing N protein.

Kits. In some embodiments, kits in accordance with the present disclosure may be used to detect, diagnose or for prognosis of MERS-CoV related disease, disorder or condition in a subject. In some embodiments, the kits comprise a container comprising one or a plurality of pharmaceutical compositions comprising IgY specific for N protein, compositions described herein and, optionally, a device used to administer the one or more pharmaceutical compositions. The disclosure provides a kit to perform any of the methods or assays described herein. In some embodiments, the kit comprises at least one container comprising a therapeutically effective amount of one or a plurality of N protein specific IgYs. In some embodiments, the IgY or IgY-based products such as conjugates are present in solution such as a buffer with adequate pH and/or other necessary additive to minimize degradation or aggregation of IgY during prolonged storage. In some embodiments, the IgYs are lyophilized for the purposes of resuspension after prolonged storage. In some embodiments, the kit optionally comprises instructions to perform any or all steps of any method described herein.

The kit may contain two or more containers, packs, or dispensers together with instructions for preparation of an array. In some embodiments, the kit comprises at least one container comprising the IgYs described herein and a second container comprising a means for maintenance, use, and/or storage of the IgY such as storage buffer or secondary antibodies that bind to IgY or that bind to N protein or indicators for antibody binding. In some embodiments, the kit comprises a composition comprising any IgY disclosed herein in solution or lyophilized or dried and accompanied by a rehydration mixture. In some embodiments, the IgYs and rehydration mixture may be in one or more additional containers.

The compositions included in the kit may be supplied in containers of any sort such that the shelf-life of the different components are preserved, and are not adsorbed or altered by the materials of the container. For example, suitable containers include simple bottles that may be fabricated from glass, organic polymers, such as polycarbonate, polystyrene, polypropylene, polyethylene, ceramic, metal or any other material typically employed to hold reagents or food; envelopes, that may consist of foil-lined interiors, such as aluminum or an alloy. Other containers include test tubes, vials, flasks, and syringes. The containers may have two compartments that are separated by a readily removable membrane that upon removal permits the components of the compositions to mix. Removable membranes may be glass, plastic, rubber, or other inert material.

Kits may also be supplied with instructional materials. Instructions may be printed on paper or other substrates, and/or may be supplied as an electronic-readable medium, such as a floppy disc, CD-ROM, DVD-ROM, zip disc, videotape, audio tape, or other readable memory storage device. Detailed instructions need not be physically associated with the kit; instead, a user may be directed to an internet web site specified by the manufacturer or distributor of the kit, or supplied as electronic mail.

In one embodiment, a kit comprises 96-well ELISA plates precoated with monospecific anti-NP IgY antibodies, washing buffer (PBS Tween), skimmed milk in PBST as blocking buffer, monoclonal antibodies specific for NP, HRP (horse radish peroxidase)-conjugate for detection of bounded antibodies, and a substrate O-phenylenediamine dihydrochloride for detection of the reaction.

Example 1

Immunization and Collection of Eggs Containing IgY

Twenty Lohmann laying hens which are 25 weeks old are bought from a local broiler farm. The animals are placed in cages, which are dedicated to broiler chickens, in groups of two animals per cage under a regimen of a 12 hr:12 hr light-dark cycle at an ambient temperature of 24±3° C. and at a relative humidity of 75±5%. Water and commercial food are offered ad libitum. Further description of Lohmann laying hens and other suitable chickens is available at hypertext transfer protocol://frabopoultry.com/wp-content/uploads/2016/10/Lohmann_LSL-Lite.pdf (last accessed Jan. 21, 2021, incorporated by reference).

Hens are divided into two immunization Groups A and B each with ten hens.

As detailed below, the ten hens in an immunization Group A are injected with 200 µg of a commercially available recombinant MERS-CoV N protein in PBS (phosphate buffered saline) in combination with an adjuvant and the ten hens in a control Group B are injected only with PBS and the adjuvant.

For Group A, recombinant N protein is emulsified at a ratio of 1:1 in complete Freund's Adjuvant ("CFA"; Sigma) and for boosts in Incomplete Freund's Adjuvant ("IFA"; Sigma) by pipetting the mixture up and down through a 19 gauge needle attached to a 5 ml syringe until a stable emulsion is formed.

On day 0 hens in Group A are immunized on the left and right side pectoral muscles with 200 µg of recombinant N protein emulsified with complete Freund's Adjuvant ("CFA"; Sigma).

On days 12 and 28, the Group A hens are boosted on the left and right side pectoral muscles with 200 µg of recombinant N protein emulsified at a ratio of 1:1 with incomplete Freund's Adjuvant ("IFA"; Sigma).

Group B hens are injected with PBS emulsified with CFA (day 0) or IFA (days 12 and 28) but no N protein on the same days as hens in Group A.

To determine antibody responses, blood samples are taken from hens in both Groups A and B before each immunization and on the last day before slaughter of the hens.

Eggs from hens in both groups are collected daily one week before and 24 hours after initial immunization. Egg collection is continued for 12 weeks. Eggs are stored at 4° C. prior to isolation of IgY isolation from the egg yolks.

IgY Separation and Purification

IgY antibodies are purified from stored eggs of Groups A and B using an EGGstract® IgY purification system from PROMEGA® according to manufacturer's instructions. Briefly, the yolks of the eggs are separated from the egg whites using an egg separator. Then a 14% polyethylene glycol (PEG6000) solution is added to the yolks at volumetric ratio 3:1. After 30 min stirring at ambient temperature (RT), the mixture is centrifuged at 5,000 g at 10° C. for 20 min. The supernatant is collected and filtered through sterile gauze.

PEG6000 is added to the filtered supernatant with gentle stirring.

The mixture is then centrifuged and 5,000 g for 20 mins.

The supernatant is collected and solid ammonium sulfate is added to precipitate proteins in the mixture which is stirred at 40° C. for 24 hrs.

The precipitate is collected by centrifugation and washed with a solution of saturated ammonium sulfate.

The washed precipitate is then dialyzed against PBS and freeze dried to obtain a powder which is stored at −20° C.

To assess the purity and molecular weight of IgY in the freeze-dried powder, samples of the power are suspended in a sodium dodecyl sulfate-polyacrylamide gel electrophoresis ("SDS-PAGE") buffer and molecular components are resolved by SDS-PAGE under reducing conditions using a 12% polyacrylamide gel with a Mini-PROTEAN® 3 cell (BIO-RAD® Laboratories, USA). The samples are mixed with 2× sample buffer boiled for 10 min at 100° C. 25 µl of the purified IgY is loaded into each well. Prestained Blue Protein Markers are used as molecular weight markers. Electrophoresis is performed at room temperature in running buffer (Tris-Glycine buffer) at 200 volts for 40 min. The protein bands are then visualized with Coomassie Brilliant Blue stain and analyzed using special software.

Example 3

Determination of Reactivity of Anti-NP IgY Antibodies by ELISA

The reactivity of samples of anti-N-protein IgY antibodies obtained as described above is determined by ELISA. Briefly, recombinant MERS-CoV N protein at a concentration of 2.5 mg/mL is contacted with ELISA plates overnight to coat the plates with the N protein. Unbound sites are blocked with skim milk after which the plates are washed. After washing 100 uL/well of the anti MERS-CoV yolk antibodies of the NP-immunized Group A and yolk antibodies from adjuvant control Group B are incubated in the plates for 90 mins and then washed.

After washing a conjugate antibody that binds to IgY antibodies is added for detection of IgY bound to the N protein on the plates.

A colorimetric substrate is used to visually determine an amount of antibody binding to the plates.

Color intensity is measured by ELISA reader and correlates with amount of N protein IgY antibodies in samples.

Example 4

Western Blotting Assay

Western blotting is performed to check the specificity of the anti MERS-COV NP IgY antibodies.

MERS-CoV N protein is fractionated on 8-12% (SDS-PAGE) and transferred to polyvinylidene difluoride (PVDF) membrane (Milipore Ltd.).

The membrane is then washed for 10 minutes in 1× tris buffered saline with 0.1% Tween-20 (TBS-T) and blocked overnight with 5% skim milk in TBS-T. Membranes are washed for 1 hour at 10-minute intervals in TBS-T.

Subsequently, the membrane is incubated with anti MERS-CoV yolk antibodies of the first and second groups and yolk antibodies from adjuvant control group for 1 hour at RT is followed by incubation with HRP-labeled goat anti-chicken IgG.

Protein detection is carried out using an HRP colorimetric detection system.

Example 5

Detection of MERS-CoV Infected Cells by Fluorescent Immunocytochemistry

MERS-CoV is inoculated on Vero cells and infected cells are harvested after 48 hours. The cells are collected by centrifugation at 1500 for 5 minutes and washed twice with wash buffer.

100 µl of the cells are added to tubes containing 200 µl of blocking buffer and are incubated for 1 hour at room temperature and then washed twice with wash buffer.

200 µl of the diluted IgY antibodies are added and incubated for 1 hour at room temperature and then washed twice with wash buffer.

100 µl of FTIC conjugated anti-chicken antibodies are added in a 1:2500 dilution and incubated for 1 hour at room temperature and then washed twice with wash buffer.

30 µl of the cell suspension is fixed on a slide and is observed under fluorescent microscope. Fluorescence indicates the presence MERS-CoV.

Example 6

Detection of MERS-COV in a Clinical Sample by Sandwich ELISA

Nasopharyngeal swabs from camels that have been confirmed infected by MERS-CoV by RT-PCR are obtained using commercially available Universal Transport Medium.

Samples are tested for the presence of, or the concentration of, MERS-CoV using ELISA in 96 well microtiter plates (Nunc).

Microtiter plates are coated with anti-NP IgY antibodies as capturing antibody in a bicarbonate buffer (pH 9.6).

Plates are then incubated overnight at 4° C. and blocked with 5% non-fat skim milk followed by washing with PBST.

Plates are incubated with clinical samples overnight at 4° C. (50 µl per well). Clinical samples previously treated with 100 µl of RIPA (radioimmunoprecipitation assay) buffer for protein extraction are incubated at 37° C. for an hour.

Rabbit anti-NP antibodies (previously prepared by the inventors) are added in an appropriate dilution as revealing antibody. Peroxidase-conjugated anti-rabbit secondary antibodies raised in goat are used as secondary antibodies.

Plates are then thoroughly washed and developed with a chromogenic substrate with the reaction stopped by addition of $H_2SO_4$. Absorbance is measured at 450 nm using microtiter plate reader where absorbance corresponds to presence or concentration of MERS-CoV in a sample.

Example 7

PCR Amplification of Gene Products of Heavy and Light IgY Chains

Seven days following a final immunization with N protein, chickens are euthanized, and spleens are harvested. Spleens are placed immediately in Trizol reagent for homogenization. The extraction of total RNAs is carried out and reversely transcribed to synthesize the first-strand cDNA using a Super Script RT kit (Invitrogen). After PCR amplification with chicken specific primers, gene products of heavy and light chain variable regions (VH and VL) are obtained and may be sequenced. The VH and VL sequences may be used to engineer antibodies by methods known in the art (for example, by a commercial service) which recognize MERS-CoV epitopes. Once the heavy- and light-chain sequences are determined, antibodies that recognize MERS-CoV can be specific modified or engineered to suit a particular diagnostic or therapeutic application, for example, to increase sensitivity or specificity or to adapt them to therapeutic administration. In some embodiments, an IgY antibody or VL or VH sequence may be humanized or adapted to administration to a camelid.

Definitions

The terms "prevention", "prevent", "preventing", "prophylaxis" and as used herein refer to a course as disclosed herein, initiated prior to the onset of a clinical manifestation of a disease state or condition, including detection of MERS-CoV, its antigens or nucleic acids, or cellular or humoral responses to MERS-CoV so as to prevent or reduce such clinical manifestation of the disease state or condition. Prevention of reduction in severity of a clinical manifestation need not be absolute to be useful, for example, it may constitute a reduction in the manifestation of >0, 5, 10, 20, 30, 40, 50, 60, 70, 80, 90, <100 or 100%

The terms "treatment", "treat" and "treating" as used herein refers a course of action such as administering an IgY-based compound or IgY-based pharmaceutical composition initiated after the onset of a clinical manifestation of a disease state or condition so as to eliminate or reduce such clinical manifestation of the disease state or condition. Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient is ill, or will be ill, as the result of a condition that is treatable by a method, IgY antibody product or pharmaceutical composition of the disclosure.

The term "in need of prevention" as used herein refers to a judgment made by a caregiver that a patient requires or will benefit from prevention. This judgment is made based on a variety of factors that are in the realm of a caregiver's expertise, but that includes the knowledge that the patient will be ill or may become ill, as the result of a condition that is preventable by a method, an IgY-based product, or pharmaceutical composition of the disclosure.

The term "individual", "subject" or "patient" as used herein refers to a human, camel including dromedary camels, bat, or other animal susceptible to infection by MERS-CoV or as a vector or carrier of MERS-CoV. It can also refer to chickens, turkeys, ducks, geese, ostridges, emus, or other avians capable of production of IgY. The term may specify male or female or both, or exclude male or female. In one aspect, the patient is an adult human. In another aspect, the patient is a non-neonate human infant. In another aspect, the patient is a human toddler, child, adolescent, or adult at least 16, 17, 18, 21, 25, 30, 40, 50, 60, 70, 80 90 or 100 years old.

The term "neonate", or newborn, refers to an infant in the first 28 days after birth. The term "non-neonate" refers to an animal older than 28 days. The methods disclosed herein are applicable to neonates or non-neonates.

The term "effective amount" as used herein refers to an amount of an agent, either alone or as a part of a pharmaceutical composition, that is capable of having any detectable, positive effect on any symptom, aspect, or characteristics of a disease state or condition. Such effect need not be absolute to be beneficial.

The term "immunize", "actively immunize", "actively immunizing", and "active immunization" means to purposefully immunize a subject, such as an avian, by exposing a subject to an antigen, for example, an antigen derived from MERS-CoV; such exposure may be carried out by exposing the subject to an intact organism, an attenuated organism, a portion of the organism such as N protein or an immunogenic segment of N protein, or a combination of the foregoing.

The term "passively immunize", "passively immunizing", and "passive immunization" means to provide antibodies against an antigen, for example, an antigen derived from MERS-CoV N protein to a subject without necessarily eliciting an immune response to the organism in the subject. Passive immunization provides immediate protection but the subject need not develop memory cells as a result.

The term "passive immunity" as used herein refers to artificially acquired immunity achieved by the transfer of antibodies to the subject.

The terms "egg" or "egg product" each mean an avian sourced whole shell egg, unfertilized egg, fertilized egg, unhatched embryo, or any product or fraction derived there-from including egg white or egg yolk. Avians include chickens, turkeys, ducks, geese, emus, and ostriches.

The term "antigen" refers to an entity or fragment thereof which can induce an immune response in an organism, particularly an animal. The term includes immunogens and regions thereof responsible for antigenicity or antigenic determinants. Antigenic determinants include peptides of sufficient length to present via MHC-I or MHC II molecules or peptides recognizable by antibodies or capable of presentation by MHC molecules, such as those at least 6, 7, 8, 9, 10, 11, 12, 13, 14, 15, 16, 17, 18, 19, 20 or >20 amino acids in length.

The term "polyclonal antibody" refers to antibodies that are heterogeneous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

The term "monospecific antibody" refers to an antibody or pool of antibodies that recognize a specific epitope, antigenic determinant, or antigen. An epitope may be unique to MERS or other coronaviruses or shared between one or more viruses expressing N protein or N protein analogs. IgY antibodies may be specific for MERS or MERS-CoV N protein or may cross-react with N proteins or N protein analogs of other coronaviruses. In some embodiments monospecific antibodies are isolated by affinity chromatography, for example, by binding to a substrate comprising an antigen, such as N protein, a domain or fragment of N protein, washing non-bound antibodies away, and elution of the antibodies bound to the antigen on the substrate. Monospecific antibodies may also be isolated or enriched by elution from a substrate to which they have bound such as a substrate comprising a peptide epitope of N protein.

The term "monoclonal antibody" is well recognized in the art and refers to an antibody that can be mass produced in the laboratory from a single clone and that recognizes only one antigen or epitope. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces large quantities of the antibody. "Monoclonal antibodies" are substantially homogenous populations of antibodies directed to a particular antigen or epitope. They may be obtained by any technique which provides for the production of antibody molecules by continuous cell lines in culture. Monoclonal antibodies may be obtained by methods known to those skilled in the art. See, for example, Kohler, et al., Nature 256:495-497, 1975, and U.S. Pat. No. 4,376, 110.

The term "crystalline" refers to an antibody, such as a monoclonal antibody that has been purified by crystallization, such as by batch crystallization. Crystalline antibodies can be used in order to generate a small volume, highly concentrated forms. See Yang et al., 2003, Crystalline antibodies for subcutaneous delivery. PNAS, 2003,100(12): 6934-6939 which is incorporated by reference. The IgY antibodies disclosed herein may be crystallized.

The term "antibody fragment" encompasses any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("scFv proteins"), and minimal recognition units consisting of the amino acid residues that mimic the hypervariable region. Antibody fragments include a portion of an antibody such as F(ab')2, F(ab)2, Fab', Fab, Fv, sFv and the like. Regardless of structure, an antibody fragment binds with the same antigen that is recognized by the intact antibody.

The term "specific binding" in the context of the characteristics of specific binding molecules, also known as specific targeted immune factors, such as an antibody or antibody fragment, refers to the ability to preferentially bind to a particular antigen that is present in a homogeneous mixture of different antigens. In certain embodiments, a specific binding interaction will discriminate between desirable and undesirable antigens (e.g., "target" and "non-target" antigens) in a sample, in some embodiments more than about 10 to 100-fold or more (e.g., more than about 1000- or 10,000-fold). In some embodiments, the specific binding molecule may specifically bind to an epitope shared among different species or strains of a virus like MERS-CoV as compared to non-shared epitopes. In certain embodiments, the affinity between an antibody and antigen when they are specifically bound in an antibody-antigen complex is characterized by a $K_D$ (dissociation constant) of less than $10^{-6}$ M, less than $10^{-7}$ M, less than $10^{-8}$ M, less than $10^{-9}$ M, less than $10^{-10}$ M, less than $10^{-11}$M, or less than about $10^{-12}$ M or less.

Terminology used herein is for the purpose of describing particular embodiments only and is not intended to be limiting of the invention.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. An antibody binding method for detecting MERS-CoV in Camelidae, comprising
obtaining a nasopharyngeal swab sample from a subject,
contacting the nasopharyngeal swab sample with a monospecific IgY antibody that recognizes MERS-CoV nucleocapsid protein ("N protein"), wherein the contacting includes contacting the sample with a calcium alginate swab to which the monospecific IgY antibody is bound, then removing a remaining unbound portion of the nasopharyngeal swab sample, and
detecting complex formation or binding of the IgY antibody to the MERS-CoV,
wherein complex formation or binding is detected with an ELISA sandwich assay, wherein the IgY antibody that recognizes MERS-CoV N protein is a capturing antibody bound to a substrate, wherein the capturing antibody bound to the substrate is contacted with the sample, and wherein complex formation is measured by the binding of a tagged secondary antibody that recognizes MERS-CoV,
wherein the substrate is a microtiter plate well or a chromatography bead,
wherein the tagged secondary antibody is bioconjugated to an enzyme.

2. The method of claim 1, wherein said sample contains no more than 20 ng/ml of MERS-CoV N protein.

3. The method of claim 1, wherein the IgY antibody is a polyclonal antibody produced by immunizing chickens with isolated or recombinant MERS-CoV N protein and recovering IgY antibody from eggs laid by the immunized chickens.

4. The method of claim 1, wherein the IgY antibody comprises a polyclonal monospecific IgY antibody for MERS-CoV N protein.

5. The method of claim 1, wherein the IgY antibody comprises a monospecific antibody that binds to a peptide epitope of MERS-CoV N protein that ranges in length from 6 to 20 amino acids of the amino acid sequence described by SEQ ID NO: 1.

6. The method of claim 1, wherein the IgY antibody comprises a monospecific antibody that binds to an N-terminal domain segment of MERS CoV N protein comprising residues 1-36 of SEQ ID NO: 1.

7. The method of claim 1, wherein the IgY antibody comprises a monospecific antibody that binds to an N-terminal domain segment of MERS CoV N protein comprising residues 37-164 of SEQ ID NO: 1.

8. The method of claim 1, wherein the IgY antibody comprises a monospecific antibody that binds to a central segment of MERS CoV N protein comprising residues 165-238 of SEQ ID NO: 1; or that binds to a disordered region or LKR containing a stretch of serine and arginine residues and comprising residues 156 to 206 of SEQ ID NO: 1 or LPKNFHIEGTGGNSQSSSRASSVSRN-SSRSSSQGSRSGNSTRGTSPGPSGI (SEQ ID NO: 3).

9. The method of claim 1, wherein the IgY antibody comprises a monospecific antibody that binds to a C-terminal domain segment of MERS CoV N protein comprising residues 239-362 of SEQ ID NO: 1.

10. The method of claim 1, wherein the IgY antibody comprises a monospecific antibody that binds to a C-terminal domain segment of MERS CoV N protein comprising residues 363-413 of SEQ ID NO: 1.

11. The method of claim 1, wherein the IgY antibody comprises a monospecific antibody that binds to one or more residues in a peptide segment of SEQ ID NO: 1 selected from the group comprising g residues 4-12, 42-47, 50-58, 60-66, 92-102, 108-126, 144-150, 172-180, 206-225, 230-240, 261-268, 296-304, 324-337, 347-353 and 399-405 described by SEQ ID NO: 1.

12. The method of claim 1, wherein the IgY antibody comprises a monospecific antibody that binds to one or more residues in a peptide segment of SEQ ID NO: 1 selected from the group comprising:
K346, W347, L348 and E349;
Y327, F328, L329, and R330;
L350, L351, E352, O353, N354, 1355, D356, A357, Y358, K359, T360, F361, P362, K363, K364, and E365;
D320, D321, H322, G323, N324, P325, and V326;
H252, K253, R254 T255, S256, T257, K258, S259, F260, N261 M262, V263, Q264, A265, F266, G267, L268, R269, G270, P271, G272, D273, L274, Q275, G276, N277, F278, G279, D280, L281, Q282, L283, N284, K285, L286, G287, T288, E289, D290, P291, and R292;
R399, P400, S401, V402, Q403, P404, G405, P406, M407, 1408, D409, V410, N411, T412, and D413;
W293, P294, 0295, 1296, A297, and E298;
F312, K313, L314, T315, H316, Q317, N318, and N319; and
L299, A300, P301, T302, A303, S304, A305, F306, M307, G308, M309, S310, and Q311.

13. The method of claim 1, wherein the IgY antibody comprises a mixture of two or more monospecific IgY antibodies to MERS CoV N protein epitopes or domains.

14. The method of claim 1, wherein the tagged secondary antibody is a peroxidase-conjugated anti-rabbit antibody.

* * * * *

SEQUENCE LISTING

```
<160> NUMBER OF SEQ ID NOS: 4

<210> SEQ ID NO 1
<211> LENGTH: 413
<212> TYPE: PRT
<213> ORGANISM: Middle East respiratory syndrome-related coronavirus

<400> SEQUENCE: 1

Met Ala Ser Pro Ala Ala Pro Arg Ala Val Ser Phe Ala Asp Asn Asn
1               5                   10                  15

Asp Ile Thr Asn Thr Asn Leu Ser Arg Gly Arg Gly Arg Asn Pro Lys
            20                  25                  30

Pro Arg Ala Ala Pro Asn Asn Thr Val Ser Trp Tyr Thr Gly Leu Thr
        35                  40                  45

Gln His Gly Lys Val Pro Leu Thr Phe Pro Pro Gly Gln Gly Val Pro
    50                  55                  60

Leu Asn Ala Asn Ser Thr Pro Ala Gln Asn Ala Gly Tyr Trp Arg Arg
65                  70                  75                  80

Gln Asp Arg Lys Ile Asn Thr Gly Asn Gly Ile Lys Gln Leu Ala Pro
                85                  90                  95
```

-continued

```
Arg Trp Tyr Phe Tyr Tyr Thr Gly Thr Gly Pro Glu Ala Ala Leu Pro
                100                 105                 110

Phe Arg Ala Val Lys Asp Gly Ile Val Trp Val His Glu Asp Gly Ala
        115                 120                 125

Thr Asp Ala Pro Ser Thr Phe Gly Thr Arg Asn Pro Asn Asn Asp Ser
    130                 135                 140

Ala Ile Val Thr Gln Phe Ala Pro Gly Thr Lys Leu Pro Lys Asn Phe
145                 150                 155                 160

His Ile Glu Gly Thr Gly Gly Asn Ser Gln Ser Ser Arg Ala Ser
                165                 170                 175

Ser Leu Ser Arg Asn Ser Ser Arg Ser Ser Gln Gly Ser Arg Ser
            180                 185                 190

Gly Asn Ser Thr Arg Gly Thr Ser Pro Gly Pro Ser Gly Ile Gly Ala
            195                 200                 205

Val Gly Gly Asp Leu Leu Tyr Leu Asp Leu Leu Asn Arg Leu Gln Ala
        210                 215                 220

Leu Glu Ser Gly Lys Val Lys Gln Ser Gln Pro Lys Val Ile Thr Lys
225                 230                 235                 240

Lys Asp Ala Ala Ala Lys Asn Lys Met Arg His Lys Arg Thr Ser
                245                 250                 255

Thr Lys Ser Phe Asn Met Val Gln Ala Phe Gly Leu Arg Gly Pro Gly
            260                 265                 270

Asp Leu Gln Gly Asn Phe Gly Asp Leu Gln Leu Asn Lys Leu Gly Thr
        275                 280                 285

Glu Asp Pro Arg Trp Pro Gln Ile Ala Glu Leu Ala Pro Thr Ala Ser
290                 295                 300

Ala Phe Met Gly Met Ser Gln Phe Lys Leu Thr His Gln Asn Asn Asp
305                 310                 315                 320

Asp His Gly Asn Pro Val Tyr Phe Leu Arg Tyr Ser Gly Ala Ile Lys
                325                 330                 335

Leu Asp Pro Lys Asn Pro Asn Tyr Asn Lys Trp Leu Glu Leu Leu Glu
            340                 345                 350

Gln Asn Ile Asp Ala Tyr Lys Thr Phe Pro Lys Lys Glu Lys Lys Gln
        355                 360                 365

Lys Ala Pro Lys Glu Glu Ser Thr Asp Gln Met Ser Glu Pro Pro Lys
    370                 375                 380

Glu Gln Arg Val Gln Gly Ser Ile Thr Gln Arg Thr Arg Thr Arg Pro
385                 390                 395                 400

Ser Val Gln Pro Gly Pro Met Ile Asp Val Asn Thr Asp
                405                 410
```

<210> SEQ ID NO 2
<211> LENGTH: 195
<212> TYPE: PRT
<213> ORGANISM: Middle East respiratory syndrome-related coronavirus
<220> FEATURE:
<221> NAME/KEY: MISC_FEATURE
<222> LOCATION: (1)..(195)
<223> OTHER INFORMATION: N terminal domain or residues

<400> SEQUENCE: 2

```
Met Ala Ser Pro Ala Ala Pro Arg Ala Val Ser Phe Ala Asp Asn Asn
1               5                   10                  15

Asp Ile Thr Asn Thr Asn Leu Ser Arg Gly Arg Gly Arg Asn Pro Lys
            20                  25                  30
```

```
Pro Arg Ala Ala Pro Asn Asn Thr Val Ser Trp Tyr Thr Gly Leu Thr
            35                  40                  45

Gln His Gly Lys Val Pro Leu Thr Phe Pro Pro Gly Gln Gly Val Pro
 50                  55                  60

Leu Asn Ala Asn Ser Thr Pro Ala Gln Asn Ala Gly Tyr Trp Arg Arg
 65                  70                  75                  80

Gln Asp Arg Lys Ile Asn Thr Gly Asn Gly Ile Lys Gln Leu Ala Pro
                 85                  90                  95

Arg Trp Tyr Phe Tyr Tyr Thr Gly Thr Gly Pro Glu Ala Ala Leu Pro
                100                 105                 110

Phe Arg Ala Val Lys Asp Gly Ile Val Trp Val His Glu Asp Gly Ala
                115                 120                 125

Thr Asp Ala Pro Ser Thr Phe Gly Thr Arg Asn Pro Asn Asn Asp Ser
130                 135                 140

Ala Ile Val Thr Gln Phe Ala Pro Gly Thr Lys Leu Pro Lys Asn Phe
145                 150                 155                 160

His Ile Glu Gly Thr Gly Gly Asn Ser Gln Ser Ser Ser Arg Ala Ser
                165                 170                 175

Ser Leu Ser Arg Asn Ser Ser Arg Ser Ser Ser Gln Gly Ser Arg Ser
                180                 185                 190

Gly Asn Ser
        195
```

<210> SEQ ID NO 3
<211> LENGTH: 51
<212> TYPE: PRT
<213> ORGANISM: Middle East respiratory syndrome-related coronavirus
<220> FEATURE:
<221> NAME/KEY: MISC_FEATURE
<222> LOCATION: (1)..(51)
<223> OTHER INFORMATION: LPK or disordered region of N protein

<400> SEQUENCE: 3

```
Leu Pro Lys Asn Phe His Ile Glu Gly Thr Gly Gly Asn Ser Gln Ser
1               5                   10                  15

Ser Ser Arg Ala Ser Ser Val Ser Arg Asn Ser Ser Arg Ser Ser Ser
                20                  25                  30

Gln Gly Ser Arg Ser Gly Asn Ser Thr Arg Gly Thr Ser Pro Gly Pro
                35                  40                  45

Ser Gly Ile
    50
```

<210> SEQ ID NO 4
<211> LENGTH: 52
<212> TYPE: PRT
<213> ORGANISM: Middle East respiratory syndrome-related coronavirus
<220> FEATURE:
<221> NAME/KEY: MISC_FEATURE
<222> LOCATION: (1)..(52)
<223> OTHER INFORMATION: N protein C terminal domain or residues

<400> SEQUENCE: 4

```
Pro Lys Lys Glu Lys Lys Gln Lys Ala Pro Lys Glu Glu Ser Thr Asp
1               5                   10                  15

Gln Met Ser Glu Pro Pro Lys Glu Gln Arg Val Gln Gly Ser Ile Thr
                20                  25                  30
```

-continued

```
Gln Arg Thr Arg Thr Arg Pro Ser Val Gln Pro Gly Pro Met Ile Asp
        35                  40                  45
Val Asn Thr Asp
 50
```